United States Patent [19]

Hirata et al.

[11] Patent Number: 4,861,718
[45] Date of Patent: Aug. 29, 1989

[54] GENE CODING FOR THERMOSTABLE BETA-GALACTOSIDASE, BACILLUS SUBTILIS HAVING THE GENE, ENZYME CODED BY THE GENE AND A PROCESS FOR THE PRODUCTION THEREOF

[75] Inventors: Haruhisa Hirata, Osaka; Hirosuke Okada, Toyonaka; Seiji Negoro, Suita, all of Japan

[73] Assignee: Wakamoto Pharmaceutical Co., Ltd., Tokyo, Japan

[21] Appl. No.: 780,842

[22] Filed: Sep. 27, 1985

[30] Foreign Application Priority Data

Sep. 29, 1984 [JP] Japan .................................. 59-202965
May 24, 1985 [JP] Japan .................................. 60-110565

[51] Int. Cl.$^4$ .......................... C12N 9/38; C12N 9/14; C12R 1/125
[52] U.S. Cl. ..................................... 435/207; 435/200; 435/839
[58] Field of Search ................................ 435/207, 200

[56] References Cited

PUBLICATIONS

Pastore, G. M. & Park, Y. K. (1979) J. Food Sci. 44(6) 1577-1579, 1588.

Ulrich, J. T., et al. (1972) J. Bacteriol, 110(2) 691-698.
European Search Report, Appln. No. 85112245.7
R. E. Goodman et al., "Chemical Abstracts", vol. 85, No. 7, Aug. 16, 1976, p. 219, abstract No. 42751f.
M. W. Griffiths et al., "Chemical Abstracts", vol. 90, No. 15, Apr. 9, 1979, p. 234, abstract No. 116931s.
S. Aiba et al., "Applied and Environmental Microbiology", vol. 46, No. 5, Nov. 1983, pp. 1059-1065.
Wakamoto Pharmaceutical Co., Ltd., "Chemical Abstracts", vol., 103, No. 9, Sep. 2, 1985, p. 181, abst. No. 66077g.
H. Hirata et al., "Chemical Abstracts", vol. 103, No. 7, Aug. 19, 1985, p. 464, abstract No. 52699z.
H. Hirata et al., "Chemical Abstracts", vol. 101, No. 25, Dec. 17, 1984, p. 175, abstract No. 223728y.

Primary Examiner—Thomas G. Wiseman
Assistant Examiner—Charles L. Patterson, Jr.
Attorney, Agent, or Firm—Wegner & Bretschneider

[57] ABSTRACT

A novel gene coding for thermostable β-galactosidase, novel recombinant DNA in which a DNA fragment containing the above gene is inserted, novel *Bacillus subtilis* in which the above recombinant DNA is introduced, and novel thermostable β-galactosidase obtained by cultivating the above *Bacillus subtilis*.

2 Claims, 7 Drawing Sheets

FIG. 3

```
AATGTGTTAT CCTCAATTTG TTACGGAGGA GATTATAACC CAGAGCAATG GCCAGAGGAA ATTGGTATG AAGATGCTAA GTTGATGCAA ATC
AAAGCGGGGG TGAATTTAGT ATCTTTAGG ATTTTCAGTT GGACCAAGAT CGAACCGTCT GATGGAGTGT TCGACTTTGA ATGGCTAGAC
AAGGTTATAG ATATACTATA TGACCACGGT GTTTATATTA ACTTGGGAC GGCGACTGCA ACTACTCCAC CTTGGTTTGT AAAAAAGTAT
CCAGATTCTT TGCCGATCGA TGAAAGCGGT GTCATTCTCT CGTTTGGCAG TAGACAACAT TATTGTCCTA ATCATCCTCA ATTAATTACG
CACATAAAGA GACTTGTGAG GGCTATAGCA GAACGGTATA AAAATCATCC GCCACTCAAA ATCTGGCATG TTAATAATGA GTATGCATGT
CACGTTTCCA AGTGTTTTTG TGAGAATTGT GCTGTCGCGT TTAGAAAGTG GCTAAAGGAA AGATATAAAA CAATCGATGA ATTAAATGAA
CGTTGGGGTA CAAACTTTTG GGGACAGCGA TACAATCATT GGGATGAAAT TAATCCCCCT AGAAAGGCAC CAACTTTTAT TAATCCATCC
CAAGAACTTG ATTACTACCG TTTTATGAAT GACTCAATTC TCAAGTTGTT TTTAACAGAA AAGGAAATTT TACGTGAGGT AACACCAGAT
ATTCCAGTAT CAACTAATTT CATCGGTTCA TTCAAACCGT TAAACTATTT TCAATGGGCT CACCATGTAG ATATTGTGAC ATGGACTCA
TATCCTGATC CCAGAGACGG CTTGCCAATT CAGCACCCCA TGATGAATGA CCTTATGCGT AGTTAAGAA AAGGTCAACC GTTTATTTG
ATGGACCAGG TAACCTCACA TGTTAACTGG CGGGATATTA ATGTTCCAAA ACCGCCAGGT GTAATGCGTC TATGGAGTTA TGCAACTATT
GCCCGTCGTG CAGATGGTAT TATGTTTTTC CAGTCGCCTC AAAGTAGAGC AGGACTGAA AAATTCCACG GTGCAATGGT GCCCCACTTT
TTGAACCAGA ATAATAGAAT TTATAGGGAA GTTACACAGT TAGGGCAAGA GCTGAAAAAG TTAGATTGTT TGGTCGGATC TAGAATCAAG
GCAGAGGTCG CGATCATTTT TGATTGGGAA AACTGGTGGG CTGTCGAACT AGGTTCCAAA CCACATAATA AACTAAGATA TATTCCTATA
GTTGAAGCTT ATTATACGGA ATTATATAAA CGTAATATAG TCTATATATTG CTGTCGATTT TGTAAGGCCA TCTGATCATC TAACAAAATA CAAAGTAGTT
ATTGCTCCAA TGTTATATAT GGTTAAAGAG GGAGAAGATG AAAACTTACG GCAATTTGTT GCTACCGGTG GCACTTTGAT TGTCAGTTTC
TTCAGTGGCA TGTAGAATGA AAATGACCGT GTACATCTAG GCGGATATCC TGCTCCTCTG CGAGATATTT TGGGGATTTT TGTTGAGGAA
TTTGTACCAT ACCCAGAAAC AAAGGTAAAC AAGCTTCTAGC GACATTTAAG GGGGATTGGT ATGCAGGACT GAATATGAT TGTACCACGT GGGCGGACAT AATCCGATTA
GAAGGGGCAG AACCTCTAGC GACATTTAAG GGGGATTGGT ATGCAGGACT TCCCGCGGT ACACGTAACT GCTACGGTAA AGGAGAGGGG
ATTTACGTCG GTACTTATCC AGATAGTAAT TATTTAGGCA GGCTTTTAGA ACAGGTTTTC GCTAAACATC ATATTAATCC CATTCTTGAA
GTAGCTGAAA ATGTAGAGGT GCAACAAAGA GAGACTGATG AATGAAGTA TTTGATTATC ATCAATCATA ATGATTACGA AGTGACCCTG
TCACTGCCAG AAGATAAGAT ATACCAGAAT ATGATTGCATG CGAAATGTTT TCGAGGAGGT GAATTGAGGA TTCAAGGGGT TGATGTAGCA
GTGTTAAGAG AGCATGATGA AGCCGGGAAG GTT
```

FIG. 4

Met-Asn-Val-Leu-Ser-Ser-Ile-Cys-Tyr-Gly-Gly-Asp-Tyr-Asn-Pro-Glu-Gln-Trp-Pro-Glu-
Glu-Ile-Trp-Tyr-Glu-Asp-Ala-Lys-Leu-Met-Gln-Lys-Ala-Gly-Val-Asn-Leu-Val-Ser-Leu-
Gly-Ile-Phe-Ser-Trp-Ser-Lys-Ile-Glu-Pro-Ser-Asp-Gly-Val-Phe-Asp-Phe-Glu-Trp-Leu-
Asp-Lys-Val-Ile-Asp-Ile-Leu-Tyr-Asp-His-Gly-Val-Tyr-Ile-Asn-Leu-Gly-Thr-Ala-Thr-
Ala-Thr-Thr-Pro-Ala-Trp-Phe-Val-Lys-Lys-Tyr-Pro-Asp-Ser-Leu-Pro-Ile-Asp-Glu-Ser-
Gly-Val-Ile-Leu-Ser-Phe-Gly-Ser-Arg-Gln-His-Tyr-Cys-Pro-Asn-His-Pro-Gln-Leu-Ile-
Thr-His-Ile-Lys-Arg-Leu-Val-Arg-Ala-Ile-Ala-Glu-Arg-Tyr-Lys-Asn-His-Pro-Ala-Leu-
Lys-Met-Trp-His-Val-Asn-Asn-Glu-Tyr-Ala-Cys-His-Val-Ser-Lys-Cys-Phe-Cys-Glu-Asn-
Cys-Ala-Val-Ala-Phe-Arg-Lys-Trp-Leu-Lys-Glu-Arg-Tyr-Lys-Thr-Ile-Asp-Glu-Leu-Asn-
Glu-Arg-Trp-Gly-Thr-Asn-Phe-Trp-Gly-Gln-Arg-Tyr-Asn-His-Trp-Asp-Glu-Ile-Asn-Pro-
Pro-Arg-Lys-Ala-Pro-Thr-Phe-Ile-Asn-Pro-Ser-Gln-Glu-Leu-Asp-Tyr-Tyr-Arg-Phe-Met-
Asn-Asp-Ser-Ile-Leu-Lys-Leu-Phe-Leu-Thr-Glu-Lys-Glu-Ile-Leu-Arg-Glu-Val-Thr-Pro-
Asp-Ile-Pro-Val-Ser-Thr-Asn-Phe-Met-Gly-Ser-Phe-Lys-Pro-Leu-Asn-Tyr-Phe-Gln-Trp-
Ala-Gln-His-Val-Asp-Ile-Val-Thr-Trp-Asp-Ser-Tyr-Pro-Asp-Pro-Arg-Glu-Gly-Leu-Pro-
Ile-Gln-His-Ala-Met-Met-Asn-Asp-Leu-Met-Arg-Ser-Leu-Arg-Lys-Gly-Gln-Pro-Phe-Ile-
Leu-Met-Glu-Gln-Val-Thr-Ser-His-Val-Asn-Trp-Arg-Asp-Ile-Asn-Val-Pro-Lys-Pro-Pro-
Gly-Val-Met-Arg-Leu-Trp-Ser-Tyr-Ala-Thr-Ile-Ala-Arg-Gly-Ala-Asp-Gly-Ile-Met-Phe-
Phe-Gln-Trp-Arg-Gln-Ser-Arg-Ala-Gly-Ala-Glu-Lys-Phe-His-Gly-Ala-Met-Val-Pro-His-
Phe-Leu-Asn-Glu-Asn-Asn-Arg-Ile-Tyr-Arg-Glu-Val-Thr-Gln-Leu-Gly-Gln-Glu-Leu-Lys-
Lys-Leu-Asp-Cys-Leu-Val-Gly-Ser-Arg-Ile-Lys-Ala-Glu-Val-Ala-Ile-Ile-Phe-Asp-Trp-
Glu-Asn-Trp-Trp-Ala-Val-Glu-Leu-Ser-Ser-Lys-Pro-His-Asn-Lys-Leu-Arg-Tyr-Ile-Pro-
Ile-Val-Glu-Ala-Tyr-Tyr-Arg-Glu-Leu-Tyr-Lys-Arg-Asn-Ile-Ala-Val-Asp-Phe-Val-Arg-
Pro-Ser-Asp-Asp-Leu-Thr-Lys-Tyr-Lys-Val-Val-Ile-Ala-Pro-Met-Leu-Tyr-Met-Val-Lys-
Glu-Gly-Glu-Asp-Glu-Asn-Leu-Arg-Gln-Phe-Val-Ala-Asn-Gly-Gly-Thr-Leu-Ile-Val-Ser-
Phe-Phe-Ser-Gly-Ile-Val-Asp-Glu-Asn-Asp-Arg-Val-His-Leu-Gly-Gly-Tyr-Pro-Gly-Pro-
Leu-Arg-Asp-Ile-Leu-Gly-Ile-Phe-Val-Glu-Glu-Phe-Val-Pro-Tyr-Pro-Glu-Thr-Lys-Val-
Asn-Lys-Ile-Tyr-Ser-Asn-Asp-Gly-Glu-Tyr-Asp-Cys-Thr-Thr-Trp-Ala-Asp-Ile-Ile-Arg-
Leu-Glu-Gly-Ala-Glu-Pro-Leu-Ala-Thr-Phe-Lys-Gly-Asp-Trp-Tyr-Ala-Gly-Leu-Pro-Ala-
Val-Thr-Arg-Asn-Cys-Tyr-Gly-Lys-Gly-Glu-Gly-Ile-Tyr-Val-Gly-Thr-Tyr-Pro-Asp-Ser-
Asn-Tyr-Leu-Gly-Arg-Leu-Leu-Glu-Gln-Val-Phe-Ala-Lys-His-His-Ile-Asn-Pro-Ile-Leu-
Glu-Val-Ala-Glu-Asn-Val-Glu-Val-Gln-Gln-Arg-Glu-Thr-Asp-Glu-Trp-Lys-Tyr-Leu-Ile-
Ile-Ile-Asn-His-Asn-Asp-Tyr-Glu-Val-Thr-Leu-Ser-Leu-Pro-Glu-Asp-Lys-Ile-Tyr-Gln-
Asn-Met-Ile-Asp-Gly-Lys-Cys-Phe-Arg-Gly-Gly-Glu-Leu-Arg-Ile-Gln-Gly-Val-Asp-Val-
Ala-Val-Leu-Arg-Glu-His-Asp-Glu-Ala-Gly-Lys-Val

FIG. 8

```
5' GGCCTATATATTTGGTTGTTTTAA
3' CCGGATATATAAACCAACAAAATT

TTAAAAATATATATTTATTTAGTA
  AATTTTTATATATAAATAAATCAT

AAATATTGTTGTTGACAAATACTAA
  TTTATAACAACAACTGTTTATGATT

ATTTTAACTTAATTTATAATTAAAC
  TAAAATTGAATTAAATATTAATTTG

GAAAATTAGCT  3'
  CTTTTAATCGA  5'
```

GENE CODING FOR THERMOSTABLE BETA-GALACTOSIDASE, BACILLUS SUBTILIS HAVING THE GENE, ENZYME CODED BY THE GENE AND A PROCESS FOR THE PRODUCTION THEREOF

BACKGROUND OF THE INVENTION

The present invention relates to a novel gene coding for thermostable beta-galactosidase, Bacillus subtilis, having the above gene, a novel enzyme coded by the gene and a process for the production thereof.

Beta-galactosidase is an enzyme which hydrolyzes lactose to galactose and glucose and is widely utilized in food processing, such as the production of milk with a low lactose content or the production of galactose or glucose from lactose contained in whey obtained in a large amount as a by-product in the production of cheese.

Generally, it is desired that enzymes for use in food processing be stable at an elevated temperature from the viewpoint of preventing microbial contamination. This also applies to the aforementioned enzyme.

Further, the enzyme is also utilized as a pharmaceutical to treat intolerance to lactose. In this case, good heat resistance is preferred for stability of the preparation as well.

The present invention has been made in order to achieve the above various requirements and provides a well-defined process for producing beta-galactosidase of excellent heat stability in a commercially advantageous manner.

DESCRIPTION OF THE RELATED ART

Thermophilic bacteria belonging to the Bacillus genus produce thermostable β-galactosidase and it is possible to obtain milk with a low lactose content by treating milk using immobilized cells of the above bacteria, as described, for instance, in the following literature references A, B and C:

A. R. E. Goodman, et al; Canadian Journal of Microbiology, 22, 817–825 (1976),

B. M. W. Griffiths, et al; Journal of the Science of Food and Agriculture, 29, 753–761 (1978), and C. T. Kobayashi, et al; Journal of Fermentation Technology, 56, 309–314 (1978).

However, those previous methods have various problems, such as low productivity of the enzyme, low affinity of the enzyme itself to the substrate, i.e. lactose, and insufficient heat stability.

The present inventors previously succeeded in introducing into *Escherichia coli* a thermostable β-galactosidase gene of *Bacillus stearothermophilus* IAM11001 via a vector by means of recombinant DNA technology and established a process for preparing the thermostable β-galactosidase by cultivating the recombinant gene [*Escherichia coli* 294-43 (pHG2), Bikoken Accession No. 7233], which was filed for a patent (Japanese Patent Application No. 171077/1983).

According to that process, highly heat-stable β-galactosidase is obtained and the enzyme can be extensively purified by simple heat treatment, which permits simplification of the purification process in commercial production. However, the process has a drawback in that the productivity of the enzyme is somewhat low.

It has become possible to produce exogenous genederived protein in large amounts using microorganisms due to the development of genetic engineering.

To use a strong promoter is one of the important requirements for expression of the gene related to such protein production by microorganism.

Significant development has been made on expression vectors containing strong promoters for a system where *E. coli* is a host, and trp promoter, lac promoter, lpp promoter, pho promoter and so on have been used.

On the other hand, although the genus Bacillus represented by *Bacillus subtilis* are hosts excellent in terms of safety, external secretion of protein etc. compared to *E. coli*, the development of expression vectors for these is considerably behind.

Concerning the preparation and utilization of expression vectors for the genus Bacillus, some prior studies can be named such as plasmid pPL608 wherein the promoter of phage spo 2 of *B. subtilis* is utilized [Gene, 16, 139 (1981)], plasmid of pGR71 series wherein an unidentified promoter on chromosomal DNA of *B. subtilis* is utilized [Molecular Cloning and Gene Regulation in Bacilli, page 311, Academic Press (1982)], and plasmid wherein the promoter of a penicillinase gene of *Bacillus bichemiformis* (pen P) is utilized [Molecular Cloning and Gene Regulation in Bacilli, page 159, Academic Press (1982)]. However, the amount of expression of exogenous gene inserted downstream of a promoter is still insufficient in all cases.

SUMMARY OF THE INVENTION

The present inventors have succeeded in introducing a thermostable β-galactosidase gene of *Bacillus stearothermophilus* (bga B) into *B. subtilis* by means of a vector utilizing gene recombination technology, and have found that such *B. subtilis* produces thermostable β-galactosidase in an amount equaling as much as 6 to 10% of cell protein.

The present inventors have, further, conducted research to develop expression vectors whose host is the genus Bacillus bacteria wherein high function of the thermostable β-galactosidase in *B. subtilis* is utilized. We have found that a promoter derived from thermophilic *Bacillus stearothermophilus* has strong promoter activity, and have elucidated the nucleotide sequence of its DNA and, further, have made it possible to produce an expression vector for the genus Bacillus appropriate for expressing desired polypeptide. In addition, the present inventors have elucidated the nucleotide sequence of the thermostable β-galactosidase gene and have also elucidated the physicochemical properties and amino acid sequence of the thermostable β-galactosidase encoded by the above nucleotide sequence.

Thus, the present invention comprises the following aspects:

(1) A gene coding for a novel thermostable β-galactosidase represented by the nucleotide sequence of FIG. 3.

(2) Novel recombinant DNA wherein a DNA fragment containing the gene represented by the nucleotide sequence of FIG. 3 is inserted into vector DNA for *B. subtilis*.

(3) Novel *B. subtilis* in which a DNA fragment containing the gene represented by the nucleotide sequence of FIG. 3 is introduced by means of a vector.

(4) A novel process for the production of the novel thermostable β-galactosidase, characterized by cultivating novel *B. subtilis* in which a DNA fragment containing the gene represented by the nucleotide sequence of FIG. 3 is introduced by means of a vector and harvesting the thermostable β-galactosidase accumulated in the cultured material.

(5) DNA having promoter activity, represented by the nucleotide sequence of FIG. 8.

(6) Novel recombinant DNA in which the DNA represented by the nucleotide sequence of FIG. 8 is inserted.

(7) A microorganism in which the novel recombinant DNA is introduced, the recombinant DNA containing the inserted DNA represented by the nucleotide sequence of FIG. 8.

(8) Novel thermostable β-galactosidase having the following physicochemical properties:

a. action and substrate specify: to hydrolyze substrates having a β-D-galactosidic linkage to release D-galactose, b. optimal pH and pH range for stability: optimal pH 5.5 pH range for stability 5.5 to 9.0 c. temperature range appropriate to activity: temperature optimal to activity about 70° C.

d. temperature range for stability: half periods of the β-galactosidase activity at 55° C., 60° C. and 65° C. are about 620, 150 and 55 hours, respectively.

e. influences of metal ions: $Mg^{++}$, $Ca^{++}$, $Cu^{++}$, $Fe^{++}$, $Co^{++}$ and $Li^+$ at a level of 1 mM do not inhibit the enzyme activity, but $Ag^+$ inhibits it by about 80% or more, and $Hg^{++}$ by about 90% or more, f. molecular weight:

(a) about 67,000 (measured by SDS-polyacrylamide electrophoresis)

(b) 78,051 (calculated from amino acid sequence)

g. Michaelis constant to lactose (km): 2.4 mM.

(9) Novel thermostable β-galactosidase according to item (8) above, having the amino acid sequence in FIG. 4.

| Lane | Sample |
|---|---|
| 1 | molecular weight marker |
| 2 | purified β-galactosidase |
| 3 | cell extract of the microorganism according to the present invention |
| 4 | the above cell extract heat treated at 70° C. for 15 minutes |
| 5 | cell extract of the host microorganism |
| 6 | the above cell extract heat treated at 70° C. for 15 minutes. |

Figure 2:
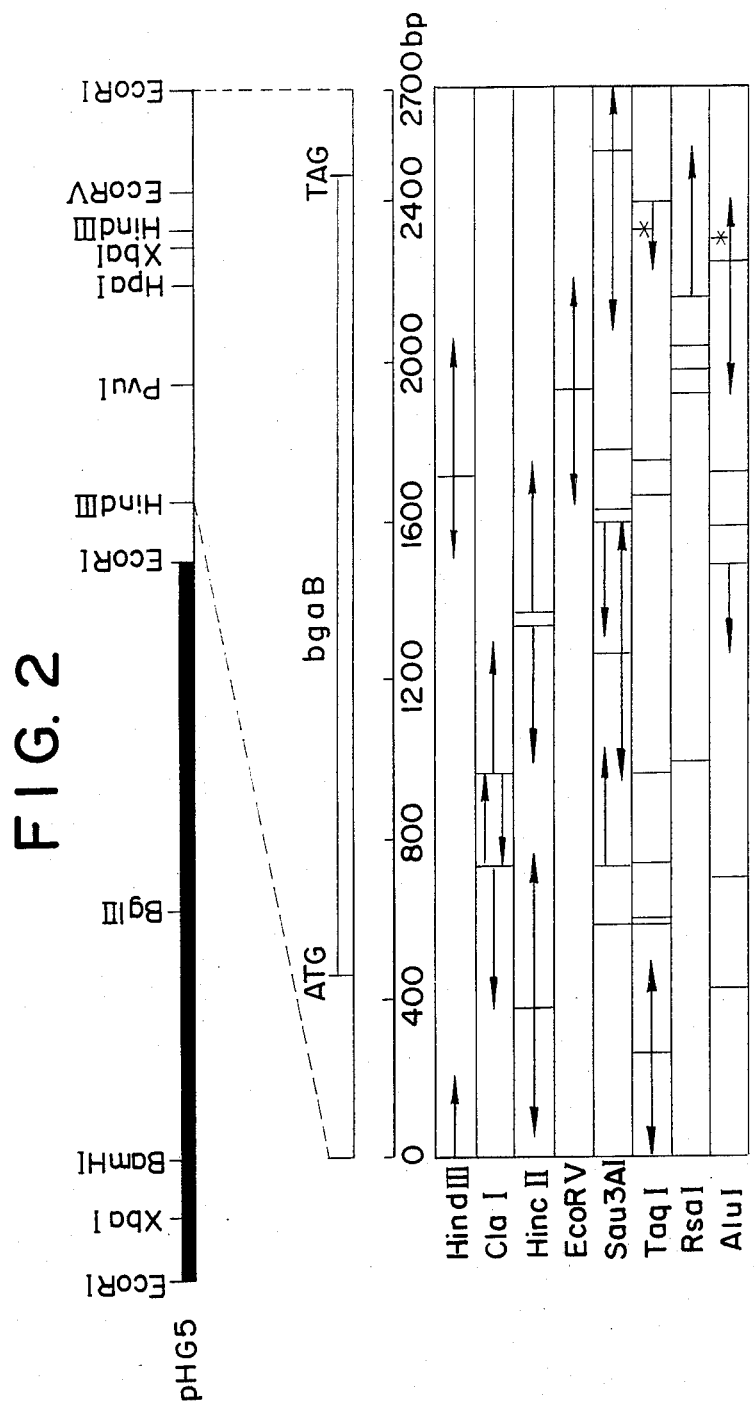

FIG. 2 shows a restriction enzyme map of novel recombinant plasmid, pHG5 according to the invention and strategy for determining the nucleotide sequence. Arrows show the directions of the nucleotide sequence determination and the lengths of the determined fragments. Only DNAs with asterisk were determined by the Maxam-Gilbert method, and the others by the dideoxy method.

FIG. 3 shows nucleotide sequence of the gene coding for the novel thermostable β-galactosidase of the present invention.

FIG. 4 illustrates amino acid sequence of the novel thermostable β-galactosidase of the present invention.

Figure 5:
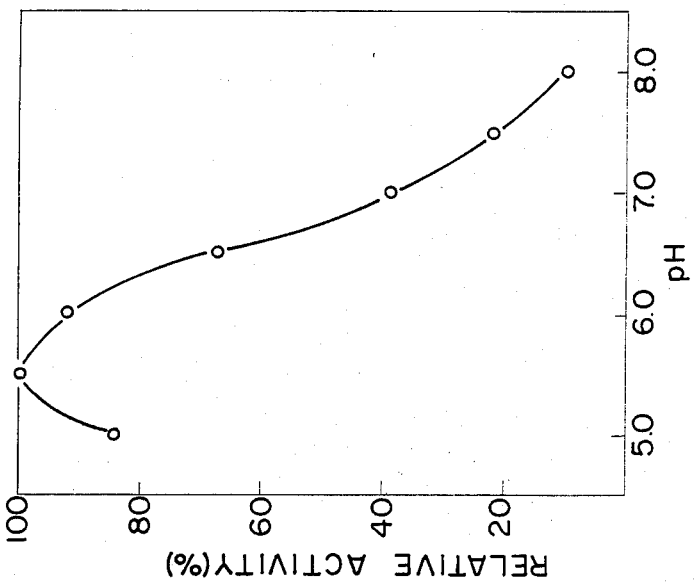

FIG. 5 shows influence of pH on the activity of the enzyme according to the present invention.

Figure 6:
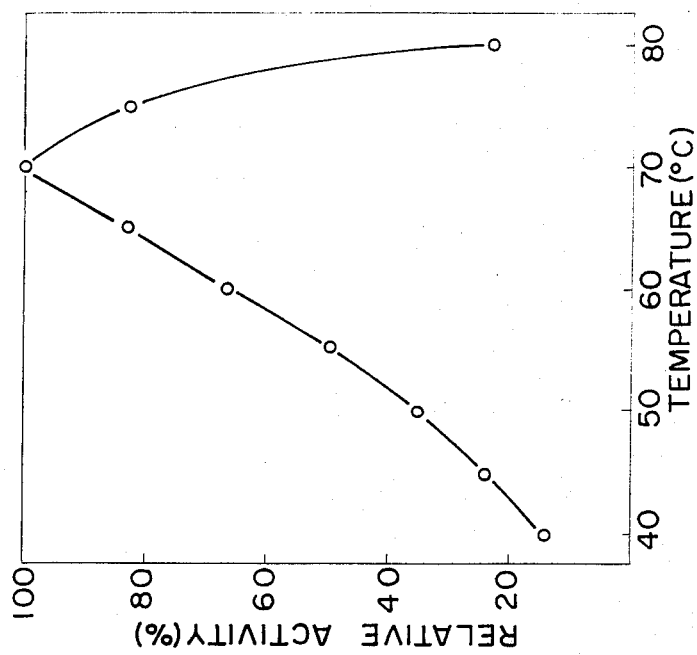

FIG. 6 illustrates influence of temperature on the stability of the enzyme according to the present invention.

Figure 7:
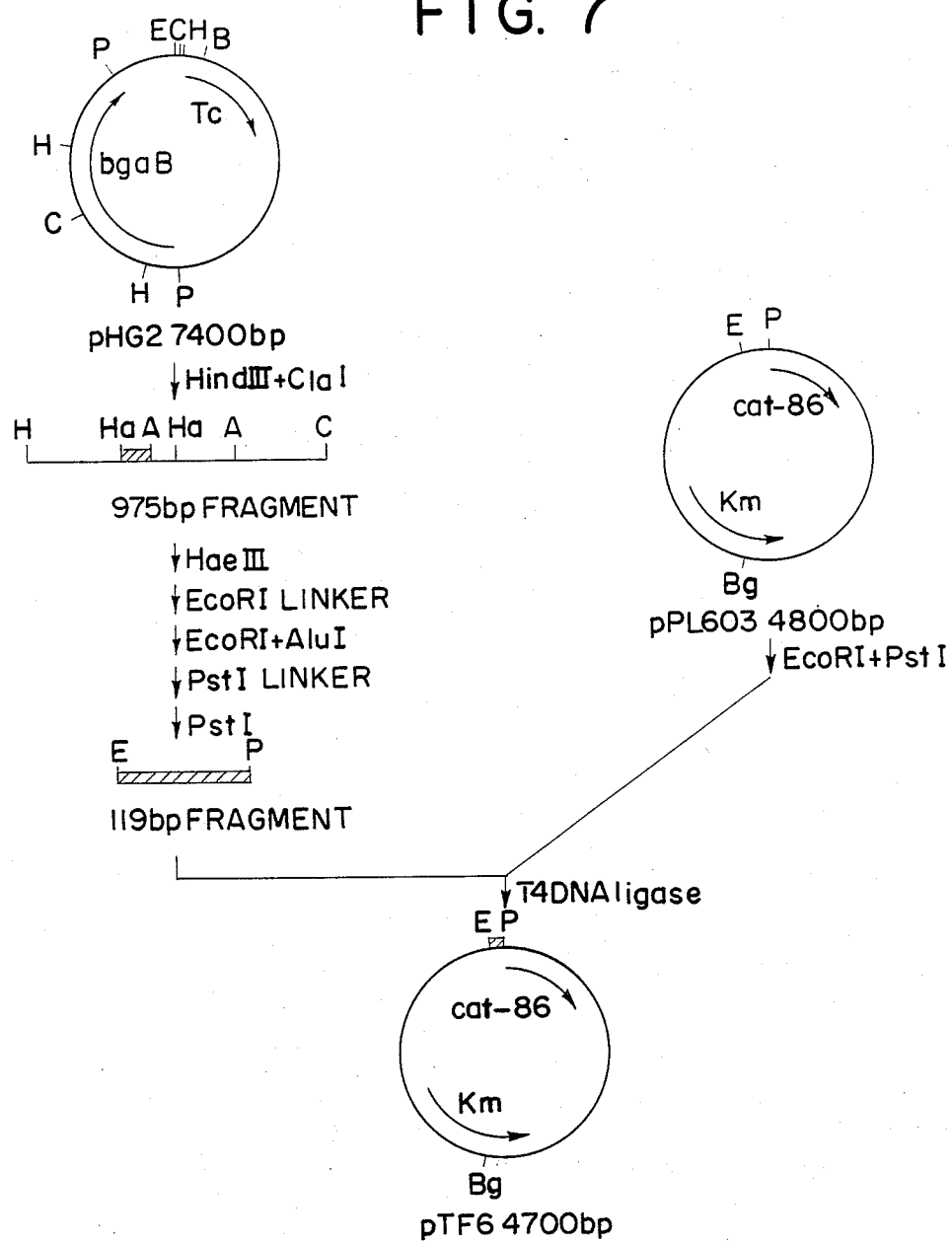

FIG. 7 shows a flow chart of a process for constructing novel recombinant DNA pTF6 of the present invention. In the figure, E represents the restriction site of Eco RI; C, Cla I; H, Hind III; P, Pst I; B, Bam HI; and Bg, Bgl II, respectively.

Tc represents a tetracycline resistant gene; Km, a kanamycin resistant gene; and cat-86, a chloramphenicol resistant gene, respectively.

FIG. 8 illustrates nucleotide sequence of DNA including a promoter region derived from thermophile, *Bacillus stearothermophilus*.

DETAILED DESCRIPTION OF THE INVENTION

In carrying out the present invention, isolation and purification of DNA carrying the genetic information of the thermostable β-galactosidase (hereinafter referred to as chromosomal DNA) from *Bacillus stearothermophilus* may be performed in a conventional manner. For instance, a phenol method as described in Biochim. Biophys. Acta. 72, 619–629 (1963) may be used.

Insertion of this chromosomal DNA into vector DNA may be performed by digesting the chromosomal DNA and the vector DNA with restriction enzymes to yield chromosomal DNA fragments and vector DNA fragments and treating the mixture of those by DNA ligases. Examples of the vector DNA used herein include pUB110, pE194, pC194, pBD9, pTP4 and pPL603.

Examples of the restriction enzymes include Bam HI, Bgl II, Eco RI, Pst I, Mlu I, Sal I and Xho I.

Further, a DNA ligase derived from T4 phage may preferably be used as a DNA ligase.

Introduction of the recombinant DNA thus obtained into *B. subtilis* may be carried out by a protoplast transformation method [Molecular and General Genetics, 168, 111–115 (1979)].

Selection of strain harboring the recombinant DNA, i.e., the vector DNA in which a DNA fragment carrying the genetic information of the thermostable β-galactosidase is inserted, depends on types of restriction enzymes and vector DNAs used in the preparation of the recombinant DNA. For instance, when Eco RI is used as a restriction enzyme and pUB110 is used as a vector DNA, this may be performed as follows.

Namely, strain is cultivated in DM3 agar medium containing 5-bromo-4-chloro-3-indolyl-β-D-galactopyranoside (hereinafter referred to as Xgal) and kanamycin. Colonies showing a blue color are selected. Finally, it is confirmed whether the β-galactosidase activity is present or absent.

Subsequently, the recombinant DNA is isolated from the obtained strain harboring the recombinant DNA. The isolation of the recombinant DNA may be performed according to a conventional manner. For instance, an alkaline extraction method may be used as described in Nucleic Acids Research, 7, 1513–1523 (1979). By introducing the recombinant DNA thus obtained into *B. subtilis*, *B. subtilis* containing the recombinant DNA may be produced. The *B. subtilis* containing the recombinant DNA can be obtained as blue colonies appearing on DM3 agar medium containing kanamycin and Xgal.

The above DM3 agar medium is prepared by sterilizing each of the following eight solutions and mixing them:

| | |
|---|---|
| (1) 4% agar | 200 ml |
| (2) 1 M sodium succinate (pH 7.3) | 500 ml |
| (3) 5% casamino acid | 100 ml |
| (4) 10% yeast extract | 50 ml |
| (5) 3.5% dipotassium hydrogen phosphate +1.5% potassium dihydrogen phosphate | 100 ml |
| (6) 20% glucose | 25 ml |
| (7) 1 M MgCl$_2$ | 20 ml |
| (8) 2% bovine serum albumin | 5 ml |

The production of the thermostable β-galactosidase according to the present invention is conducted by cultivating the novel B. subtilis carrying the recombinant gene obtained above in a conventional manner, harvesting it, lysing the cells in a conventional manner and, subsequently, obtaining an extract with no debris. Purification of the thermostable β-galactosidase thus obtained is carried out by heat treatment or a usual purification process of protein such as ion exchange chromatography, gel filtration etc. Heat treatment is particularly effective. This method of purification by heat treatment differs from previous methods for obtaining thermostable β-galactosidase from *Bacillus stearothermophilus* or *Thermus thermophilus* and is a novel and effective method.

That is, since all proteins produced by thermophiles are generally heat-stable, whole protein are gradually denatured but it does not happen that only β-galactosidase is purified when a cell extract is heat treated.

In contrast, the β-galactosidase produced by the novel microorganism of the present invention, wherein a gene of a thermophile is inserted into a mesophile, *B. subtilis*, is remarkably more thermostable than the protein of the original *B. subtilis*, so that most of the protein of *B. subtilis* are denatured and aggregated by heat treatment at a temperature of 65° C. to 75° C., preferably about 70° C., for about 15 to about 30 minutes while the β-galactosidase is scarcely denatured and remains soluble in a heat treated liquid.

Merely by centrifuging the heat treated liquid to remove heat-denatured insoluble material, β-galactosidase with an increased purity is obtained in a supernatant liquid.

This convenient and effective method of purification of β-galactosidase by heat treatment is a novel technique, which is first made possible by the gene recombination technology according to the present invention.

The present invention will further be explained in detail by Examples below.

In the following Examples, *Escherichia coli* 294-43 (pHG2) (Bikoken Accession No. 7233), i.e., *E. coli* harboring recombinant plasmid pHG2 in which a DNA fragment carrying the genetic information of thermostable β-galactosidase of *Bacillus stearothermophilus* IAM 11001 was inserted, was used as a DNA doner; pUB110 was used as vector DNA; and publicly known *B. subtilis, Bacillus subtilis* MI 111 [T. IMANAKA, et al, Journal of Bacteriology, 146, 1091–1097 (1981)], was used as host *B. subtilis*, by way of example.

EXAMPLE 1

Preparation and digestion of plasmid DNA carrying genetic information of thermostable β-galactosidase

*Escherichia coli* 294-43 (pHG2) was cultivated on 150 ml of M9 medium (Na$_2$HPO$_4$ 5.8 g/l, KH$_2$PO$_4$ 3 g/l, NaCl 5 g/l, NH$_4$Cl 1 g/l, CaCl$_2$ 11 mg/l, MgSO$_4$ 95 mg/l, FeCl$_3$ 1.6 mg/l, casamino acid 5 g/l, and glucose 4 g/l) at 37° C. until absorbance of the culture liquid at 600 nm was 0.6 to 1.0, then 200 μg/ml of chloramphenicol was added and cultivation was continued overnight. After collecting and washing, the cells were dispersed in 15 ml of a solution containing 25 mM Tris-HCl (pH 8.0), 5 mM glucose, 10 mM EDTA, and 2 mg/mlo lysozyme, left at 0° C. for 30 minutes, and then 30 ml of 1% SDS (sodium lauryl sulfate) containing 0.2N NaOH was added so that the cells were lysed, and then left at 0° C. for 5 minutes. Then, 22.5 ml of a solution of 3M sodium acetate (pH 4.8) was added and left at 0° C. for 1 hour, and then centrifuged (8000 rpm, 20 minutes) to yield a supernatant liquid. Ethanol in a volume 2.5 times the volume of the supernatant liquid was added to the supernatant liquid to precipitate DNA, which was then dissolved in 5 ml of a solution containing 10 mM Tris-HCl (pH 7.5) and 1 mM EDTA (hereinafter referred to as TE buffer solution). This DNA solution was subjected to centrifuging to equilibrium in cesium chloride-ethidium bromide density gradients to yield 500 μg of pHG2 plasmid. In order to divide the plasmid DNA into vector DNA and chromosonal DNA of *B. stearothermophilus* carrying the genetic information of the thermostable β-galactosidase, 5 μg of the DNA was digested with 5 units of Pst 1 in 50 μl of a reaction liquid containing 20 mM Tris-HCl (pH 7.5), 10 mM MgCl$_2$, 50 mM (NH$_4$)$_2$SO$_4$ and 0.1 mg/ml bovine serum albumin at 37° C. for 3 hours. Subsequently, the Pst I was inactivated by heating at 65° C. for 10 minutes and the DNA was precipitated by ethanol, which was then dissolved in 20 μl of the TE buffer solution.

EXAMPLE 2

Change of terminals of a DNA fragment carrying the genetic information of thermostable β-galactosidase from Pst I site to Eco RI site In order to connect the DNA fragment carrying the genetic information of the thermostable β-galactosidase obtained in Example 1 to vector DNA pUB110, Pst I sites on both terminals of the DNA fragment were changed to Eco RI sites in the following manner. 5 μg of the Pst I-digested DNA obtained in Example 1 was digested with 0.2 U of exonuclease BAL-31 (obtained from New England Biolabs Co.) in 25 μl of a reaction liquid containing 20 mM Tris-HCl (pH 8.0), 660 mM NaCl, 12 mM CaCl$_2$ and 1 mM EDTA at 30° C. for 6 minutes. The BAL-31 was inactivated by phenol treatment. After ethanol precipitation, the precipitate was dissolved in the TE buffer solution. To this was added 25 p mol of Eco RI linker (GGAATTCC) (obtained from Takara Shuzo Co.) in which 5′ terminus was phosphatized with T4-polynucleotidekinase, which was then digested with 1 U of T4-DNA ligase in 40 μl of a reaction liquid containing 66 mM Tris-HCl (pH 7.5), 10 mM MgCl$_2$, 10 mM dithiothreitol and 1 mM ATP at 15° C. for 16 hours. After the T4-DNA ligase was deactivated at 65° C. for 20 minutes, 60 μl of the reaction liquid provided with 14 μl of the TE buffer solution and 6 μl of 1M Nacl was digested with 50 U of Eco RI at 37° C. for 3 hours. After inactivation of the Eco Ri by heating at 65° C. for 20 minutes, ethanol precipitation was performed and the precipitate was dissolved in 40 μl of the TE buffer solution.

EXAMPLE 3

Preparation and digestion of vector DNA

DNA of pUB 110 plasmid was prepared as follows. Bacillus subtilis MI 111, (pUB 110), B. subtilis harboring pUB 110 as plasmid was cultivated with shaking on 500 ml of L medium (trypton 1%, yeast extract 0.5%, NaCl 0.5% and glucose 0.2%, pH 7.0) at 37° C. until absorbance of the culture liquid at 600 nm was 2 to 3. After collecting and washing, the cells were dispersed in 50 ml of a solution containing 25 mM Tris-HCl (pH 8.0), 50 mM glucose, 10 mM EDTA and 2 mg/ml lysozyme and left at 37° C. for 30 minutes. 100 ml of a solution containing 0.2M NaOH and 1% SDS was added to lyse the cells and left at 0° C. for 5 minutes. Then, 75 ml of a solution of 3M sodium acetate (pH 4.8) was added, left at 0° C. for 1 hour and centrifuged (8000 rpm, 20 minutes) to yield a supernatant liquid.

Ethanol in a volume 2.5 times the volume of the supernatant liquid was added to the supernatant liquid to precipitate DNA, which was then dissolved in 5 ml of the TE buffer solution. This DNA solution was subjected to centrifuging to equilibrium in cesium chloride-ethidium bromide density gradients to yield 50 μg of pUB 110 plasmid DNA. In order to digest the vector DNA, 1 μg of pUB 110 was digested with 5 U of Eco RI at 37° C. for 2 hours in 75 μl of a reaction liquid containing 10 mM Tris-HCl (pH 7.5), 100 mM NaCl and 10 mM $MgCl_2$. After heating at 65° C. for 10 minutes, DNA was precipitated by ethanol and dissolved in 10 μl of the TE buffer solution.

EXAMPLE 4

Insertion of DNA fragment carrying genetic information of thermostable β-galactosidase 5 μg of the Eco RI fragment of DNA obtained in Example 2 and 1 μg of the Eco RI fragment of vector DNA obtained in Example 3 were mixed together and ligated with 0.2 U of T4-DNA ligase in 50 μl of a reaction liquid containing 66 mM Tris-HCl (pH 7.5), 10 mM $MgCl_2$, 10 mM dithiothreitol and 1 mM ATP at 4° C. for 16 hours. The T4-DNA ligase was inactivated by heating at 65° C. for 10 minutes and the DNA was precipitated by ethanol, which was then dissolved in 100 μl of the TE buffer solution to yield a DNA solution.

EXAMPLE 5

Transformation of B. subtilis by recombinant plasmid and selection of B. subtilis having an ability to produce thermostable β-galactosidase Bacillus subtilis MI 111 was cultivated on 20 ml of a Penassay broth (beef extract 0.15%, yeast extract 0.15%, peptone 0.5%, glycose 0.1%, NaCl 0.3%, dipotassium hydrogen phosphate 0.37% and potassium dihydrogen phosphate 0.13%, pH 7.0) with shaking at 37° C. until absorbance at 570 nm was 0.8 to 1.0, and then harvested. This was dispersed in 2.5 ml of a SMMP solution (a mixture of a double concentrated SMM solution and a quadruple concentrated Penassay broth in equal amounts) containing 2 mg/ml lysozyme and maintained with gentle shaking at 37° C. for 2 hours to prepare protoplast. The protoplast was collected by centrifuging (4000 rpm, 15 minutes), washed with a SMMP solution, again centrifuged and dispersed in 2 ml of a SMMP solution.

The SMM solution herein is a mixture solution comprising 0.5M sucrose, 20 mM maleic acid (pH 6.5) and 20 mM $MgCl_2$.

0.5 ml of the above protoplast suspension was added to a mixture of 30 μl of the DNA solution obtained in Example 4 and 30 μl of a double concentrated SMM solution, followed by addition of 1.5 ml of a 40% polyethylene glycol solution (each 100 ml containing 40 g of polyethylene glycol 6000 and 50 ml of a double concentrated SMM solution). This was left for 2 minutes and 5 ml of a SMMP solution was added, and the protoplast then recovered by centrifuging. The protoplast was suspended in 1 ml of an SMMP solution, cultivated at 30° C. for 1.5 hours with shaking, and then spread on DM3 agar medium (carrying 1 mg/ml of kanamycin and 40 μg/ml of Xgal) for regeneration. After cultivation at 37° C. for 2 days, colonies of B. subtilis having an ability to produce β-galactosidase showed a blue color.

The novel B. subtilis thus obtained was designated Bacillus subtilis MI 111 (pHG5) and deposited in the Research Institute of Biological Industrial Technology, the Agent of Industrial Technology, with the accession number Bikoken Accession No. 7831. A second deposit has been made with the accession number FERM BP-911.

The microbiological properties of this novel B. subtilis, Bacillus subtilis MI 111 (pHG5) are substantially the same as those of common B. subtilis, except that the former shows resistance to kanamycin and an ability to produce thermostable β-galactosidase.

Therefore, a usual cultivation method can be adopted. Hereinafter, only one embodiment will be illustrated by way of example.

EXAMPLE 6

Production and heat stability test of β-galactosidase

Bacillus Subtilis MI 111 (pHG5) was cultivated on 150 ml of LL medium (tripton 1%, yeast extract 0.5%, NaCl 0.5% and lactose 0.2%, pH 7.0) containing 5 μg/ml kanamycin with shaking at 37° C. for 16 hours, harvested, and then suspended in 3 ml of a Z buffer solution (0.1M phosphate buffer (pH 7.0), 10 mM KCl, 1 mM $MgSo_4$ and 50 mM 2-mercaptoethanol). This was sonicated and centrifuged (15,000 rpm, 15 minutes). The supernatant liquid thus obtained was used as a cell extract.

β-galactosidase activity of this cell extract before and after heat treatment at 70° C. for 30 minutes was measured using 0-nitrophenol-β-D-galactopyranoside (hereinafter referred to as ONPG) as a substrate in the following manner.

2 ml of a Z buffer solution containing 0.08 mg/ml of ONPG and 0.4 ml of the enzyme solution was mixed, left at 65° C. for a given period of time, and after addition of 1 ml of 1M $Na_2CO_3$, cooled by ice. The amount of 0-nitrophenol generated by a reaction was determined through absorbance at 420 nm. 1 U was defined as the amount of enzyme liberating 1 μmol of 0-nitrophenol in 1 minute.

For comparison, Escherichia coli 294-43 (pHG2) was cultivated on an LL medium containing tetracycline (5 μg/ml), from which a cell extract was obtained as described above. Bacillus stearothermophilus IAM 11001 was also cultivated on LL medium at 55° C. and a cell extract was obtained. Those cell extracts were tested in the same way as described above.

The results are shown in Table 1.

TABLE 1

| β-galactosidase activity of cell extract | Present invention Bacillus subtilis MI 111 (pHG5) | Comparison 1 Escherichia coli 294-43 (pHG2) | Comparison 2 Bacillus stearothermophilus IAM 11001 |
| --- | --- | --- | --- |
| (Immediately after extraction) Activity (U/ml) | 310 | 12.0 | 42.0 |
| Specific activity (U/mg protein) | 22 | 0.53 | 1.7 |
| (After heat treatment at 70° C., 30 min) Activity (U/ml) | 280 | 9.7 | 14 |
| Specific activity (U/mg protein) | 70 | 2.4 | 1.0 |
| Ratio of remaining activity (%) | 90 | 81 | 33 |
| Relative increase in specific activity (times) | 3.2 | 4.5 | 0.8 |

As can be seen in Table 1, β-galactosidase of the present invention and Comparison 1 show the ratios of remaining activity of 90% and 81%, respectively, after heat treatment at 70° C. for 30 minutes, which are very high values and mean excellent heat stability compared with the ratio of remaining activity of 33% in Comparison 2.

As to purification efficiency of each enzyme by heat treatment, the specific activities of the present invention and Comparison 1 were increased by 3.2 times and 4.5 times, respectively, while that of Comparison 2 was decreased by 0.8 times.

As can be seen from productivity of thermostable enzyme of each microorganism (activity U/ml) after heat treatment), yield was increased by 29 times by the present invention based on Comparison 1 or by 20 times based on Comparison 2.

Further, in order to examine purification efficiency of the enzyme by heat treatment in more detail, cell extracts from the microorganism according to the present invention, i.e., Bacillus subtilis MI 111 (pHG5), its host microorganism, Bacillus subtilis MI 111 (pUB 110) and extracts obtained by heat treating the above extracts at 70° C. for 15 minutes were subjected to SDS-polyacrylamide gel electrophoresis [U.K. Laemmli, Nature 227, 680–685 (1970)].

In these tests, purified β-galactosidase was used as a standard, and a mixture of RNA-polymerase (165000, 155000, 39000), bovine serum albumin (68000) and a trypsin inhibitor (21500) was used as marker proteins for molecular weight determination. After electrophoresis, 0.02% Coomassie Brilliant Blue R250 (ICI) was used for staining. Results are shown in FIG. 1.

Figure 1:
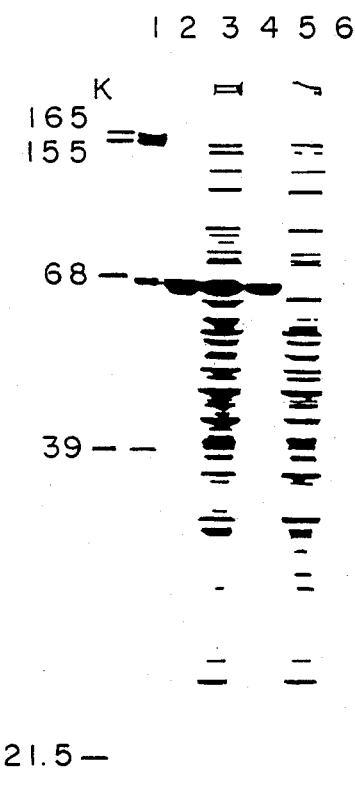
FIG. 1 shows the results of SDS-polyacrylamide gel electrophoresis. Each lane corresponds to the following.

Lanes 1 to 6 in FIG. 1 correspond to the following:

| Lane | Sample |
| --- | --- |
| 1 | marker proteins for molecular weight determination |
| 2 | purified β-galactosidase |
| 3 | cell extract of the microorganism according to the invention |
| 4 | the above cell extract heat treated at 70° C. for 15 min. |
| 5 | cell extract of the host microorganism |
| 6 | the above cell extract heat treated at 70° C. for 15 min. |

As can be seen from FIG. 1, the cell extract of the microorganism according to the present invention (lane 3) and the cell extract of the host microorganism (lane 5) contain substantially the same various components, except that the former contains β-galactosidase but the latter does not.

These various components other than β-galactosidase disappeared almost completely in samples which were heat treated at 70° C. for 15 minutes (lanes 4 and 6).

In another experiment, a half period of the activity of purified β-galactosidase according to the present invention has been determined, and it has been found that the half period at 60° C. is 150 hours, which is much longer than the 7 minutes described in the literature A and the 450 minutes described in the literature B.

Physiocochemical properties of the enzyme and test methods will now be explained below in detail.

(1) Action and substrate specificity;
Substrates having a β-D-galactoside bond were hydrolyzed to liberate D-galactose.

Typical substrates include lactose, i.e., 4-O-β-D-galactopyranosyl-D-glucopyranose, ONPG, and P-nitrophenol β-D-galactopyranoside.

(2) Optimal pH and pH range for stability; Optimal pH: 5.5 (see FIG. 5) pH range for stability: 5.5 to 9.0

The optimal pH was determined from measured values of the enzyme activity in McIlvaine's buffer. The pH range for stability was determined from measured values of enzyme activity remaining after heat treatment in McIlvaine's buffer at various pHs at 60° C. for 90 minutes.

Each measured value was expressed as a ratio to the maximum value (relative activity ratio and remaining activity ratio). However, glycine-sodium hydroxide buffer was used instead of McIlvaine's buffer in measurements on the condition of pH above 7.5.

(3) Temperature range appropriate to activity; Optimal temperature for activity: about 70° C. (see FIG. 6)

This value was obtained from enzyme activities measured in McIlvaine's buffer (pH 5.5) at various temperatures.

(4) Temperature range for stability;
Stability to temperature is shown in Table 2.

For instance, a half period at 60° C. is 150 hours, which means excellent heat stability.

These values were half periods of enzyme activity measured in McIlvaine's buffer (pH 7.0) at various temperatures.

TABLE 2

| Temperature (°C.) | Half period of β-galactosidase activity (hours) |
| --- | --- |
| 55 | 620 |
| 60 | 150 |
| 65 | 55 | influences of metal ions;
Influences of metal ions are shown in Table 3.
Activity was particularly inhibited by silver ions and mercury ions.

TABLE 3

| Metal ions (1 mM) | Relative activity (%) |
| --- | --- |
| no metal | 100 |
| $Mg^{++}$ | 103 |
| $Ca^{++}$ | 100 |
| $Cu^{++}$ | 102 |
| $Fe^{++}$ | 108 |

TABLE 3-continued

| Metal ions (1 mM) | Relative activity (%) |
|---|---|
| Co++ | 103 |
| Li+ | 102 |
| Ag+ | 16.6 |
| Hg++ | 2.2 |

Each ion was added in a predetermined concentration to a reaction system of ONPG substrate, from which the activity of enzyme was determined, and the value obtained was expressed as percentages based on the value in the case of no metal ion (relative activity) in Table 3.

(6) Molecular weight; about 67,000 was determined by the aforementioned SDS-polyacrylamide gel electrophoresis (see FIG. 1).

Further, molecular weight of 240,000 to 250,000 was obtained by a gel filtration method using a TSK G3000 SW column (Toyo Soda Co., Ltd.), therefore this value seems to be affected by enzyme association.

(7) Michaelis constant to lactose;

A Michaelis constant (Km) to a lactose substrate was determined by Lineweaver-Burk plots [Buichi Horio and Jinpei Yamashita, ediors, "Basic Experimental Methods of Proteins and Enzymes" Nankodo, 387 (1981)]. Km was found to be 2.4 mM.

This value is remarkably low compared with Km values of commercially available enzymes, L, O and G, 43.1 mM, 39.4 mM and 26.6 mM, respectively, which suggests that substrate affinity of the present enzyme to lactose is very large.

EXAMPLE 7

Analysis of recombinant DNA pHG5 contained in *B. subtilis* and nucleotide sequence of gene coding for thermostable β-galactosidase The transformant obtained in Example 5 was cultivated on 500 ml of L medium containing kanamycin (5 μg/ml) at 37° C. and 50 μg of plasmid DNA was obtained in a similar way to Example 3. Using this plasmid DNA, *Bacillus subtilis* MI 111 was transformed similarly to Example 5. All the transformants obtained were resistant to kanamycin and had an ability to produce β-galactosidase.

This means that a DNA fragment carrying the genetic information of β-galactosidase was inserted into the plasmid DNA.

This plasmid DNA was digested with a restriction enzyme, Eco RI, in a similar way to Example 2 and subjected to 1% agarose gel electrophoresis to determine the size of the DNA fragment carrying the genetic information of thermostable β-galactosidase. The size was found to be 2.9 kilobase pair (kb).

Nucleotide sequence of the gene coding for thermostable β-galactosidase present in the above EcoRI fragment was determined by the dideoxy methods [F. Sanger, et al, Proceedings of the National Academy of Science of the U.S.A., 74, 5463 (1977)] and the Maxam-Gilbert method [A. M. Maxam and W. Gilbert, Methods in Enzymology, 65, 499 (1980)].

FIG. 3 shows the determined nucleotide sequence of the gene coding for the thermostable β-galactosidase, and FIG. 2 shows a restriction enzyme map of recombinant DNA pHG5 and strategy of the determination of the nucleotide sequence.

FIG. 4 shows the amino acid sequence of polypeptide to be translated after ATG translation initiation codon on the above nucleotide sequence.

The following experiments support a finding that the polypeptide represented by the amino acid sequence of FIG. 4 is identical with the thermostable β-galactosidase of the present invention.

(1) The amino acid sequence from the N-terminal of the polypeptide of FIG. 4 completely corresponded to the fourteen amino acids sequence from the N-terminal of the purified thermostable β-galactosidase according to the present invention which was obtained by Edman-degradation: Met-Asn-Val-Leu-Ser-Ser-Ile-Cys-Tyr-Gly-Gly-Asp-Tyr-Asn.

(2) The amino acid composition of the polypeptide of FIG. 4 was compared with amino acid composition determined by hydrochloric acid hydrolysis of the purified thermostable β-galactosidase of the present invention, and both coincided with each other closely except for unstable Trp and Cys, as shown in Table 4

TABLE 4

| Amino acid | Predicted from DNA sequence | HCl hydrolysis of β-galactosidase |
|---|---|---|
| Lys | 38 | 38.4 |
| His | 19 | 17.5 |
| Trp | 21 | 7.0 |
| Arg | 36 | 35.9 |
| Asx | 78 | 75.2 |
| Thr | 25 | 25.7 |
| Ser | 29 | 29.3 |
| Glx | 72 | 73.8 |
| Pro | 37 | 32.6 |
| Gly | 43 | 45.8 |
| Ala | 36 | 36.9 |
| Cys | 10 | 2.5 |
| Val | 49 | 49.4 |
| Met | 15 | 14.2 |
| Ile | 48 | 46.5 |
| Leu | 52 | 53.0 |
| Tyr | 35 | 33.6 |
| Phe | 29 | 27.9 |

Amino acids constituting polypeptide are herein abbreviated as listed in Table 5.

TABLE 5

| Met | Methionine | Ile | Isoleucine |
|---|---|---|---|
| Ala | Alanine | Leu | Leucine |
| Arg | Arginine | Lys | Lysine |
| Asn | Asparagine | Phe | Phenylalanine |
| Asp | Aspartic acid | Pro | Proline |
| Cys | Cysteine | Ser | Serine |
| Gln | Glutamine | Thr | Threonine |
| Glu | Glutamic acid | Trp | Tryptophan |
| Gly | Glycine | Tyr | Tyrosine |
| His | Histidine | Val | Valine |

Isolation of DNA containing bgaB promoter region will be explained.

Selection of strain harboring the recombinant DNA depends on types of restriction enzymes and vector DNAs used in the preparation of the recombinant DNA. For instance, when Eco RI is used as a restriction enzyme and pPL603 is used as a vector, cat-86 gene located downstream of bgaB promoter will be expressed by this promoter and, therefore, the envisaged colony will be selected as a colony capable of growing on DM3 agar medium containing chloramphenicol and kanamycin.

Then, recombinant DNA may be isolated from the recombinant DNA strain thus obtained by an alkaline extraction method [Nucleic Acids Research 7, 1513

(1979)]. Insertion of this DNA may be confirmed by determining nucleotide sequence by the dideoxy method [Science, 214, 1205 (1981)].

Another aspect of the present invention will be explained concretely by the Examples below.

In the following Examples, *Escherichia coli* 294-43 (pHG2) harboring plasmid pHG2, in which bgaB gene was cloned (Bikoken Accession No. 7233) was used as a DNA doner; pPL 603 [Journal of Bacteriology, 146, 1162 (1981)] was used as a vector DNA; and *Bacillus subtilis* RM 125 [Molecular and General Genetics, 152, 65 (1977)]:(preserved in the Bacillus Genetic Stock Center, Ohio State University, as *Bacillus subtilis* 1A253 and available to anybody) was used as a host microorganism, by way of example.

EXAMPLE 8

Isolation of DNA containing a promoter of bgaB gene

*Escherichia coli* 294-43 (pHG2) was cultivated on 150 ml of M9 medium (Na$_2$HPO$_4$ 5.8 g/l, KH$_2$PO$_4$ 3 g/l, NaCl 5 g/l, NH$_4$Cl 1 g/l, CaCl$_2$ 11 mg/l, MgSO$_4$ 95 mg/l, FeCl$_3$ 1.6 mg/l, casamino acid 5 g/l and glucose 4 g/l) at 37° C. until absorbance of the cultivation liquid at 600 nm was 0.6 to 1.0 and, after addition of 200 μg/ml of chloramphenicol, the cultivation was contained overnight. After harvesting and washing, the cells were dispersed in 15 ml of a solution containing 25 mM Tris-HCl (pH 8.0), 50 mM glucose, 10 mM EDTA and 2 mg/ml lysozyme, left at 0° C. for 30 minutes and 30 ml of 1% SDS (sodium lauryl sulfate) containing 0.2N NaOH was added to lyse the cells, and then left at 0° C. for 5 minutes. Then, 22.5 ml of a solution of 3M sodium acetate (pH 4.8) was added, the mixture left at 0° C. for one hour and then centrifuged (8000 rpm, 20 minutes) to yield a supernatant liquid. Ethanol in a volume 2.5 times the volume of the supernatant liquid, was added to the supernatant liquid to precipitate DNA, which was then dissolved in 5 ml of a solution containing 10 mM Tris-HCl (pH 7.5) and 1 mM EDTA (hereinafter referred to as TE buffer solution). This DNA solution was subjected to centrifuging to equilibrium in cesium chloride-ethidium bromide density gradients to yield 500 μg of pHG2.

In order to isolate the DNA containing a promoter of bga B gene (107 bp Hae III-Alu I fragment), 200 U of Hind III and 120 U of Cla I were added to 100 μg of pHG2, which were then digested in 320 μl of a reaction liquid containing 10 mM Tris-HCl (pH 8.0), 10 mM MgCl$_2$, 50 mM NaCl and 1 mM dithiothreitol at 37° C. for 4 hours and subjected to 4% polyacrylamide gel electrophoresis, 13 μg of Hind III-Cla I fragment of 975 bp being recovered.

36 U of Hae III was added to 13 μg of the 975 bp Hind III-Cla I fragment, which was then digested in 50 μl of a reaction liquid containing 10 mM Tris-HCl (pH 7.5), 10 mM MgCl$_2$, 50 mM NaCl and 1 mM dithiothreitol at 37° C. for 3 hours and then heated at 70° C. for 10 minutes to inactivate Hae III.

To this was added 250 pmol of Eco RI linker pGGAATTCC (produced by Takara Shuzo Co.) whose 5' terminus was phosphatized by T4 polynucleotide kinase, which were then ligated by 125 U of T4 DNA ligase in 100 μl of a reaction liquid containing 66 mM Tris-HCl (pH 7.5), 10 mM MgCl$_2$, 10 mM dithiothreitol and 1 mM ATP at 15° C. for 16 hours.

After T4 DNA ligase was inactivated by heating at 65° C. for 20 minutes followed by addition of 4 μl of 1M NaCl, 104 μl of the reaction liquid was treated with 60 U of Eco RI and 48 U of Alu I at 37° C. for 4 hours.

After Eco RI and Alu I were inactivated by heating at 70° C. for 10 minutes, 200 pmol of Pst I linker pGCTGCAGC (produced by Takara Shuzo Co.) whose 5' terminus was phosphatized by T4 polynucleotide kinase was added to the above, which was then ligated by 150 U of T4 DNA ligase in 200 μl of a reaction liquid containing 66 mM Tris-HCl (pH 7.5), 10 mM MgCl$_2$, 10 mM dithiothreitol and 1 mM AP at 15° C. for 16 hours.

After T4 DNA ligase was inactivated by heating at 65° C. for 20 minutes followed by addition of 20 μl of 1M NaCl, 210 μl of the reaction liquid was treated with 60 U of Pst I at 37° C. for 3 hours.

This DNA solution was fractionated by 5% polyacrylamide gel electrophoresis and 1.5 μg of 119 bp Eco RI-Pst I fragment was recovered.

EXAMPLE 9

Preparation and Digestion of vector DNA

DNA of pPL 603 resistant to kanamycin was prepared as follows.

Publicly known *Bacillus subtilis* harboring pPL 603 as plasmid, *Bacillus subtilis* IE 31 (obtained from the Bacillus Genetic Stock Center, Ohio State University), was cultivated with shaking on 500 ml of L medium (trypton 1%, yeast extract 0.5%, NaCl 0.5% and glucose 0.2%, pH 7.0) at 37° C. until absorbance of the culture liquid at 600 nm was 2 to 3. After harvesting and washing, the cells were dispersed in 50 ml of a solution containing 25 mM Tris-HCl (pH 8.0), 50 mM glucose, 10 mM EDTA and 2 mg/ml lysozyme and left at 37° C. for 30 minutes. 100 ml of 1% SDS containing 0.2M NaOH was added to lyse the cells and left at 0° C. for 5 minutes. Then, 75 ml of 3M sodium acetate (pH 4.8) was added, left at 0° C. for one hour, and then centrifuged (8000 rpm, 20 minutes) to yield a supernatant liquid. Ethanol in a volume 2.5 times the volume of the supernatant liquid was added to the supernatant liquid to precipitate DNA, which was then dissolved in 5 ml of TE buffer. This DNA solution was subjected to centrifuging to equilibrium in cesium chloride-ethidium bromide density gradients to yield 50 μg of pPL 603 plasmid DNA.

In order to digest the vector DNA, 10 U of Eco RI and 5 U of Pst I were added to 2.2 μg of pPL 603, which was digested in 25 μl of a reaction liquid containing 50 mM Tris-HCl (pH 7.5), 10 mM MgCl$_2$, 100 mM NaCl and 1 mM dithiothreitol at 37° C. for 2 hours. Eco RI and Pst I were inactivated by heating at 70° C. for 10 minutes.

EXAMPLE 10

Ligation of DNA fragment containing bga B promoter and vector DNA 0.5 μg of the DNA fragment obtained in Example 8 and 0.5 μg of the vector DNA obtained in Example 9 were ligated in 35 μg of a reaction liquid containing 66 mM Tris-HCl (pH 7.5), 10 mM MgCl$_2$, 10 mM dithiothreitol and 1 mM ATP with T4 DNA ligase at 15° C. for 16 hours. By carrying out the above procedures, the recombinant molecule pTF6 was obtained.

The outline of the procedure described above is shown in FIG. 7.

EXAMPLE 11

Transformation of B. subtilis by recombinant DNA

Bacillus subtilis RM 125 was cultivated with shaking on 20 ml of Penassay broth (beef extract 0.15%, yeast extract 0.15%, peptone 0.5%, glucose 0.1%, NaCl 0.3%, dipotassium hydrogen phosphate 0.37% and potassium dihydrogen phosphate 0.13%, pH 7.0) at 37° C. until absorbance at 570 nm was 0.8 to 1.0, and harvested. The cells were suspended in 2.5 ml of a SMMP solution (a mixture of a double concentrated SMM solution and quadruple concentrated Penassay broth in equal amounts) and gently shaken at 37° C. for 2 hours to prepare protoplast. The protoplast was collected by centrifuging (4000 rpm, 15 minutes), washed with an SMMP solution, centrifuged again and dispersed in 2 ml of an SMMP solution.

The above SMM solution was a mixture containing 0.5M sucrose, 20 mM maleic acid (pH 6.5) and 20 mM $MgCl_2$.

To a mixture of 35 μl of the DNA (plasmid pTF6) solution obtained in Example 10 and 35 μl of a double concentrated SMM solution were added 0.5 ml of the above protoplast dispersion and 1.5 ml of a 40% polyethylene glycol solution which contained 40 g of polyethylene glycol 6000 and 50 ml of a double concentrated SMM solution in 100 ml, and left for 2 minutes. 5 ml of an SMMP solution was added and the protoplast was recovered by centrifuging. This protoplast was dispersed in 1 ml of an SMMP solution, cultivated with shaking at 30° C. for 1.5 hours, and then coated on DM3 agar medium for regeneration containing kanamycin (1 mg/ml) and chloramphenicol (10 μg/ml). After cultivation at 37° C. for 2 days, Bacillus subtilis harboring the recombinant DNA was obtained which was resistant to both antibiotics, kanamycin and chloramphenicol.

The novel B. subtilis thus obtained was designated Bacillus subtilis RM 125 (pTF6).

Further, microbiological properties of this B. subtilis RM 125 (pTF6) are identical with those of usual B. subtilis except that the former is resistant to kanamycin and chloramphenicol.

EXAMPLE 12

Analysis of structure of recombinant plasmid

Preparation of recombinant plasmid from B. subtilis RM 125 (pTF6) was performed as describe in Example 9.

2 μg of pTF6, was digested with 5 U of Eco RI and 5 U of Pst I in 50 μl of a reaction liquid containing 50 mM Tris-HCl (pH 7.5), 10 mM $MgCl_2$, 100 mM NaCl and 1 mM dithiothreitol at 37° C. for 2 hours. Sizes of the resultant two DNA fragments were determined by 5% polyacrylamide gel electrophoresis and 1% agarose gel electrophoresis. The sizes were 4600 bp and 119 bp, respectively.

Then, nucleotide sequence of the DNA fragment of 119 bp was determined by a dideoxy method, and it was confirmed that it had a structure such that Eco RI linker and Pst I linker were ligated to Hae III site and Alu I site, respectively of the 107 bp fragment containing bga B promoter.

TEST EXAMPLE

Comparison of a yield of cat-86 gene product (chloramphenicol acetyltransferase) expressed by bga promoter Bacillus subtilis RM 125 (pTF6) was cultivated on 50 ml of Penassay broth containing 5 μg/ml chloramphenicol and 1% glucose at 37° C. for 20 hours with shaking and, after harvesting, dispersed in 5 ml of 0.1M Tris-HCl (pH 7.8). After sonication and centrifuging (15,000 rpm, 15 minutes), the resultant supernatant was used as a cell extract.

Chloramphenicol acetyltransferase (hereinafter referred to as CAT) activity of the cell extract was determined by the specthrophotometric method of Shaw [W. V. Shaw, Methods in Engymology, 43,737 (1975)], and found to be 17 U/mg protein.

Bacillus subtilis RM 125 harboring pPL 603 was cultivated in a similar procedure and CAT activity of the obtained cell extract was 0.052 U/mg protein. Therefore, the yield of CAT was increased by about 300 times by the introduction of bga B promoter.

We claim:
1. Thermostable β-galactosidase having the following physicochemical properties:
   a. action and substrate specificity: to hydrolyse substrates having a β-D-galactosidic linkage to release D-galactose,
   b. optimal pH and pH range for stability: optimal pH 5.5 pH range for stability 5.5 to 9.0
   c. temperature range appropriate for activity: optimal temperature for activity about 70° C.
   d. temperature range for stability: half periods of the β-galactosidase activity at 55° C., 60° C. and 65° C. are about 620, 150 and 55 hours, respectively,
   e. influences of metal ions: $Mg^{++}$, $Ca^{++}$, $Cu^{++}$, $Fe^{++}$, $Co^{++}$ and $Li^+$ at a level of 1 mM do not inhibit the enzyme activity but $Ag^+$ inhibits the activity by about 80% or more, and $Hg^{++}$ by about 90% or more,
   f. molecular weight:
   (a) about 67,000 (measured by SDS-polyacrylamide electrophoresis)
   (b) 78,051 (calculated from amino acid sequence)
   g. Michaelis constant to lactose (Km): 2.4 mM.
2. Thermostable β-galactosidase according to claim 1, characterized by having amino acid sequence of FIG. 4.

* * * * *